(12) United States Patent
Czeizler et al.

(10) Patent No.: US 12,138,476 B2
(45) Date of Patent: Nov. 12, 2024

(54) MACHINE LEARNING-BASED GENERATION OF 3D DOSE DISTRIBUTIONS FOR VOLUMES NOT INCLUDED IN A TRAINING CORPUS

(71) Applicant: Siemens Healthineers International AG, Steinhausen (CH)

(72) Inventors: Elena Czeizler, Helsinki (FI); Mikko Hakala, Rajamaki (FI); Shahab Basiri, Siuntio (FI); Hannu Laaksonen, Espoo (FI); Maria Cordero Marcos, Espoo (FI); Christopher Boylan, Helsinki (FI); Jarkko Peltola, Tuusula (FI); Ville Pietila, Helsinki (FI); Esa Kuusela, Espoo (FI)

(73) Assignee: Siemens Healthineers International AG, Steinhausen (CH)

( * ) Notice: Subject to any disclaimer, the term of this patent is extended or adjusted under 35 U.S.C. 154(b) by 525 days.

(21) Appl. No.: 17/485,794

(22) Filed: Sep. 27, 2021

(65) Prior Publication Data
US 2023/0095485 A1    Mar. 30, 2023

(51) Int. Cl.
*A61N 5/10* (2006.01)
*G06N 3/08* (2023.01)
(Continued)

(52) U.S. Cl.
CPC .......... *A61N 5/1031* (2013.01); *A61N 5/1039* (2013.01); *G06N 3/08* (2013.01); *G16H 20/40* (2018.01); *G16H 50/20* (2018.01)

(58) Field of Classification Search
CPC ................ A61N 5/1031; A61N 5/1039; A61N 2005/1041; G06N 3/08; G16H 20/40; G16H 50/20
See application file for complete search history.

(56) References Cited

U.S. PATENT DOCUMENTS 10,449,388 B2 * 10/2019 Yin ........................ A61N 5/103
10,734,118 B2 *  8/2020 Moore ................ A61N 5/1031
11,813,479 B2 * 11/2023 Czeizler ................ A61N 5/103

OTHER PUBLICATIONS

Fan, Jiawei et al., "Automatic treatment planning based on three-dimensional dose distribution predicted from deep learning technique", Medical Physics, vol. 46, No. 1, Nov. 28, 2018 (Nov. 28, 2018), pp. 370-381.

(Continued)

*Primary Examiner* — Mark R Gaworecki
(74) *Attorney, Agent, or Firm* — Fitch, Even, Tabin & Flannery LLP

(57) ABSTRACT

A radiation treatment plan three-dimensional dose prediction machine learning model is trained using a training corpus that includes a plurality of radiation treatment plans that are not specific to a particular patient and wherein the training corpus includes some, but not all, possible patient volumes of interest. Information regarding the patient (including information regarding at least one volume of interest for the patient that was not represented in the training corpus) is input to the radiation treatment plan three-dimensional dose prediction machine model. The latter generates predicted three-dimensional dose distributions that include a predicted three-dimensional dose distribution for the at least one volume of interest that was not represented in the training corpus.

20 Claims, 3 Drawing Sheets

(51) Int. Cl.
*G16H 20/40* (2018.01)
*G16H 50/20* (2018.01)

(56) References Cited

OTHER PUBLICATIONS

Chan, Maria F. et al., "A Review and Analysis of Managing Commonly Seen Implanted Devices for Patients Undergoing Radiation Therapy", Advances in Radiation Oncology, vol. 6, No. 4, Jul. 1, 2021 (Jul. 1, 2021), p. 100732.
PCT Search Report and Written Opinion from related International Application No. PCT/EP2022/076653, dated Feb. 3, 2023, 15 pages.

* cited by examiner

MACHINE LEARNING-BASED GENERATION OF 3D DOSE DISTRIBUTIONS FOR VOLUMES NOT INCLUDED IN A TRAINING CORPUS

TECHNICAL FIELD

These teachings relate generally to treating a patient's planning target volume with radiation pursuant to a radiation treatment plan and more particularly to generating a radiation treatment plan for that patient.

BACKGROUND

The use of radiation to treat medical conditions comprises a known area of prior art endeavor. For example, radiation therapy comprises an important component of many treatment plans for reducing or eliminating unwanted tumors. Unfortunately, applied radiation does not inherently discriminate between unwanted materials and adjacent tissues, organs, or the like that are desired or even critical to continued survival of the patient. As a result, radiation is ordinarily applied in a carefully administered manner to at least attempt to restrict the radiation to a given target volume. A so-called treatment plan often serves in the foregoing regards.

A radiation treatment plan typically comprises specified values for each of a variety of treatment-platform parameters during each of a plurality of sequential fields. Treatment plans for radiation treatment sessions are often generated through a so-called optimization process. As used herein, "optimization" will be understood to refer to improving a candidate treatment plan without necessarily ensuring that the optimized result is, in fact, the singular best solution. Such optimization often includes automatically adjusting one or more treatment parameters (often while observing one or more corresponding limits in these regards) and mathematically calculating a likely corresponding treatment result to identify a given set of treatment parameters that represent a good compromise between the desired therapeutic result and avoidance of undesired collateral effects.

In many cases optimization is carried out as a function of one or more optimization objectives. One approach for choosing appropriate values for optimization objectives includes training a knowledge-based model to predict such values. While helpful, such an approach often provides only a partial solution because such models typically do not provide objectives for portions of a patient's body that were not included in the initially trained model.

BRIEF DESCRIPTION OF THE DRAWINGS

The above needs are at least partially met through provision of the machine learning-based generation of 3D dose distributions for volumes not included in a training corpus described in the following detailed description, particularly when studied in conjunction with the drawings, wherein.

Figure 1:
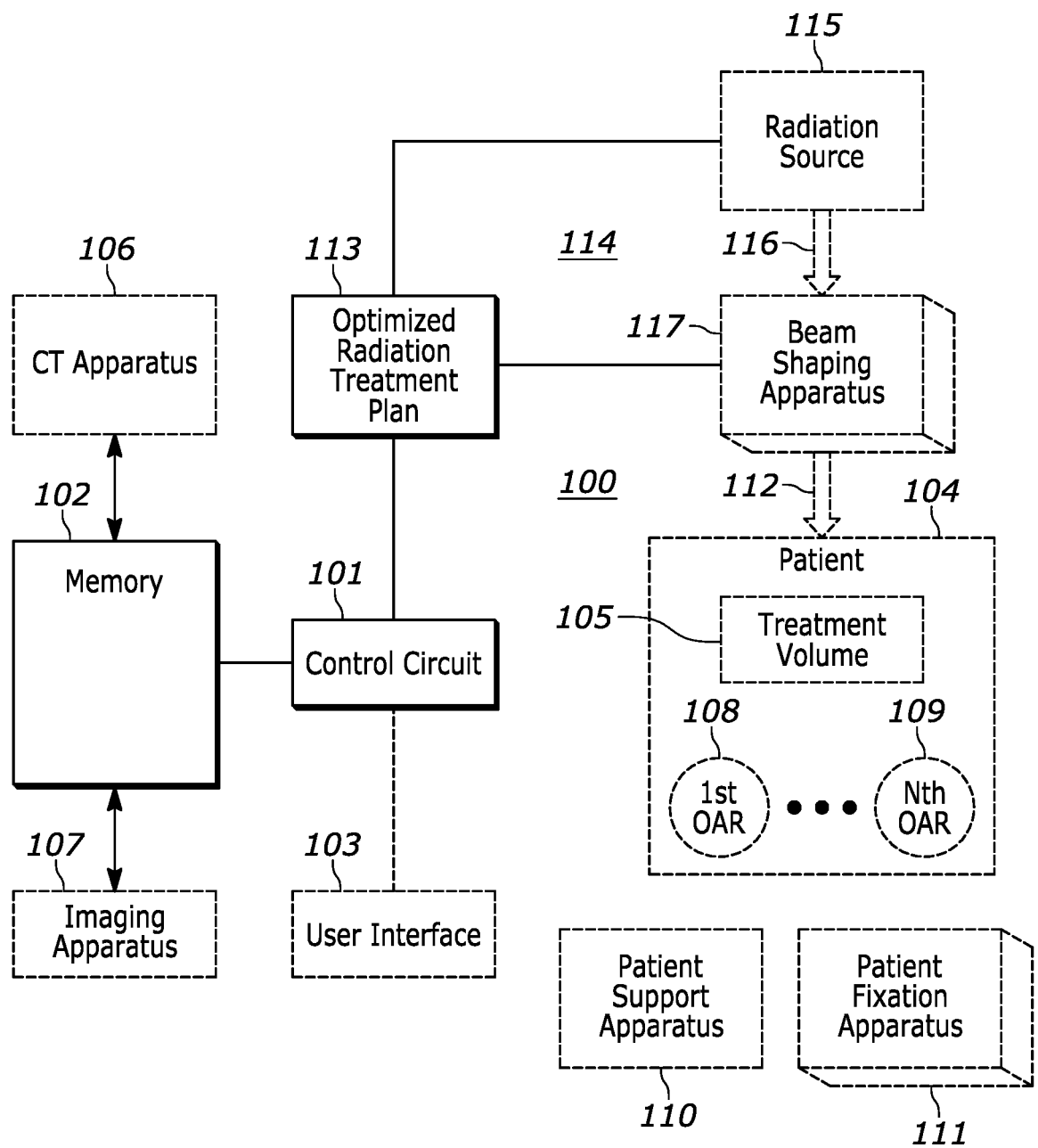
FIG. 1 comprises a block diagram as configured in accordance with various embodiments of these teachings.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present teachings. Also, common but well-understood elements that are useful or necessary in a commercially feasible embodiment are often not depicted in order to facilitate a less obstructed view of these various embodiments of the present teachings. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein. The word "or" when used herein shall be interpreted as having a disjunctive construction rather than a conjunctive construction unless otherwise specifically indicated.

DETAILED DESCRIPTION

Generally speaking, these various embodiments provide a radiation treatment plan three-dimensional dose prediction machine learning model that facilitates generating a radiation treatment plan for a particular patient. By one approach this model is trained using a training corpus that includes a plurality of radiation treatment plans that are not specific to the patient and wherein the training corpus includes some, but not all, possible patient volumes of interest. These teachings also provide information regarding the patient, wherein the patient information includes information regarding at least one volume of interest for the patient that was not represented in the training corpus. Information regarding the patient is input to the radiation treatment plan three-dimensional dose prediction machine model. The latter then generates predicted three-dimensional dose distributions that include a predicted three-dimensional dose distribution for the at least one volume of interest that was not represented in the training corpus.

By one approach, the aforementioned radiation treatment plan three-dimensional dose prediction machine learning model comprises a neural network machine learning model such as, but not limited to, a convolutional neural network.

By one approach, the aforementioned information regarding the patient may comprise at least one computed tomography image, at least one patient treatment volume contour, at least one organ-at-risk contour, and field geometry information pertaining to the treatment platform.

If desired, these teachings will further support generating at least one dosimetric parameter for the at least one volume of interest for the patient, which volume was not represented in the training corpus, as a function of the predicted three-dimensional dose distribution. That dosimetric parameter may comprise, for example, at least one of a dose volume histogram, maximum dose levels within a given contour, a minimum dose level for a target structure, mean dose levels within a given contour, dose-volume points, a homogeneity index for target coverage, a generalized equivalent uniform dose, and/or a conformity index.

By one approach, these teachings will further comprise automatically generating an optimization objective for the at least one volume of interest for the patient that was not represented in the training corpus as a function of the predicted three-dimensional dose distribution for the at least one volume of interest for the patient that was not represented in the training corpus. A radiation treatment plan can then be optimized for the patient as a function of that optimization objective and therapeutic radiation administered to the patient as a function of the optimized radiation treatment plan.

These teachings are flexible and highly practical in practice. Accordingly, these teachings will accommodate various modifications and supplemental aspects. As but one illustrative example in these regards, the information regarding the patient may include information regarding a non-biological structure. In such a case, the training corpus may not include that non-biological structure. Nevertheless, these teachings will accommodate inputting the information regarding the non-biological structure to the radiation treatment plan three-dimensional dose prediction machine learning model and generating predicted three-dimensional dose distributions that include a predicted three-dimensional dose distribution for the non-biological structure.

So configured, these teachings permit providing optimization objectives for portions of a patient's body that were not included in an initially trained model. These teachings can also provide objectives for optimization helper structures created by the planner during the planning phase (including, for example, ring structures, contours defined by certain isodose lines, or contours defined by the planner based on proximity to selected organs-at-risk). These teachings are also applicable for application settings characterized by several small patient treatment volume contours inside a much larger organ-at-risk (as can occur when the patient presents multiple small tumors inside the brain, lung, or liver).

These and other benefits may become clearer upon making a thorough review and study of the following detailed description. Referring now to the drawings, and in particular to FIG. 1, an illustrative apparatus 100 that is compatible with many of these teachings will first be presented.

In this particular example, the enabling apparatus 100 includes a control circuit 101. Being a "circuit," the control circuit 101 therefore comprises structure that includes at least one (and typically many) electrically-conductive paths (such as paths comprised of a conductive metal such as copper or silver) that convey electricity in an ordered manner, which path(s) will also typically include corresponding electrical components (both passive (such as resistors and capacitors) and active (such as any of a variety of semiconductor-based devices) as appropriate) to permit the circuit to effect the control aspect of these teachings.

Such a control circuit 101 can comprise a fixed-purpose hard-wired hardware platform (including but not limited to an application-specific integrated circuit (ASIC) (which is an integrated circuit that is customized by design for a particular use, rather than intended for general-purpose use), a field-programmable gate array (FPGA), and the like) or can comprise a partially or wholly-programmable hardware platform (including but not limited to microcontrollers, microprocessors, and the like). These architectural options for such structures are well known and understood in the art and require no further description here. This control circuit 101 is configured (for example, by using corresponding programming as will be well understood by those skilled in the art) to carry out one or more of the steps, actions, and/or functions described herein.

The control circuit 101 operably couples to a memory 102. This memory 102 may be integral to the control circuit 101 (as when the memory 102 and control circuit 101 are both included on a shared integrated circuit) or can be physically discrete (in whole or in part) from the control circuit 101 as desired. This memory 102 can also be local with respect to the control circuit 101 (where, for example, both share a common circuit board, chassis, power supply, and/or housing) or can be partially or wholly remote with respect to the control circuit 101 (where, for example, the memory 102 is physically located in another facility, metropolitan area, or even country as compared to the control circuit 101).

In addition to optimization objectives information, patient geometry information, field geometry information, and so forth this memory 102 can serve, for example, to non-transitorily store the computer instructions that, when executed by the control circuit 101, cause the control circuit 101 to behave as described herein. (As used herein, this reference to "non-transitorily" will be understood to refer to a non-ephemeral state for the stored contents (and hence excludes when the stored contents merely constitute signals or waves) rather than volatility of the storage media itself and hence includes both non-volatile memory (such as read-only memory (ROM) as well as volatile memory (such as a dynamic random access memory (DRAM).)

By one optional approach the control circuit 101 also operably couples to a user interface 103. This user interface 103 can comprise any of a variety of user-input mechanisms (such as, but not limited to, keyboards and keypads, cursor-control devices, touch-sensitive displays, speech-recognition interfaces, gesture-recognition interfaces, and so forth) and/or user-output mechanisms (such as, but not limited to, visual displays, audio transducers, printers, and so forth) to facilitate receiving information and/or instructions from a user and/or providing information to a user.

By one approach, a computed tomography apparatus 106 and/or other non-CT imaging apparatus 107 as are known in the art can source some or all of any desired patient-related imaging information.

In this illustrative example the control circuit 101 is configured to output an optimized radiation treatment plan 113. This radiation treatment plan 113 typically comprises specified values for each of a variety of treatment-platform parameters during each of a plurality of sequential fields. In this case the radiation treatment plan 113 is generated through an optimization process. Various non-automated, automated, or partially-automated optimization processes specifically configured to generate such a radiation treatment plan are known in the art. As the present teachings are not overly sensitive to any particular selections in these regards, further elaboration in these regards is not provided here except where particularly relevant to the details of this description.

By one approach the control circuit 101 can operably couple to a radiation treatment platform 114 that is configured to deliver therapeutic radiation 112 to a corresponding patient 104 in accordance with the optimized radiation treatment plan 113. These teachings are generally applicable for use with any of a wide variety of radiation treatment platforms. In a typical application setting the radiation treatment platform 114 will include a radiation source 115. The radiation source 115 can comprise, for example, a radio-frequency (RF) linear particle accelerator-based (linac-based) x-ray source, such as the Varian Linatron M9. The linac is a type of particle accelerator that greatly increases the kinetic energy of charged subatomic particles or ions by subjecting the charged particles to a series of oscillating electric potentials along a linear beamline, which can be used to generate ionizing radiation (e.g., X-rays) 116 and high energy electrons.

A typical radiation treatment platform 114 may also include one or more support apparatuses 110 (such as a couch) to support the patient 104 during the treatment session, one or more patient fixation apparatuses 111, a gantry or other movable mechanism to permit selective movement of the radiation source 115, and one or more beam-shaping apparatuses 117 (such as jaws, multi-leaf collimators, and so forth) to provide selective beam shaping and/or beam modulation as desired. As the foregoing elements and systems are well understood in the art, further elaboration in these regards is not provided here except where otherwise relevant to the description.

Figure 2:
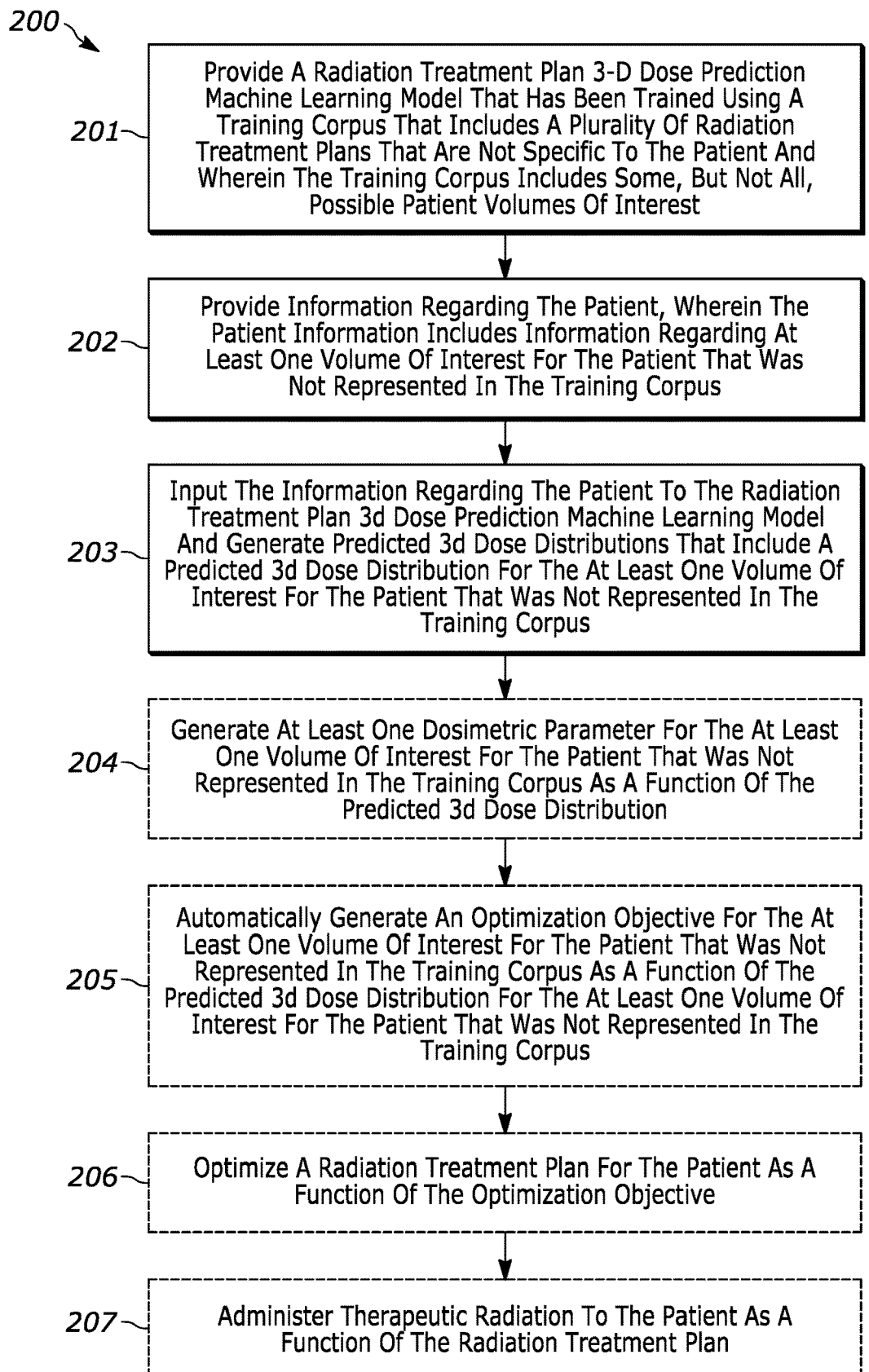
FIG. 2 comprises a flow diagram as configured in accordance with various embodiments of these teachings.

Referring now to FIG. 2, a process 200 that can be carried out, for example and at least in part, by the above-described control circuit 101 will be presented.

At block 201, this process 200 provides a radiation treatment plan three-dimensional dose prediction machine learning model. Various machine learning models are known in the art. For the sake of an illustrative example, it will be presumed here that this machine learning model comprises a neural network machine learning model, and in particular, a convolutional neural network.

In this example this radiation treatment plan three-dimensional dose prediction machine learning model has been trained using a training corpus that includes a plurality of radiation treatment plans that are not specific to the patient. These radiation treatment plans, for example, may comprise, in whole or in part, optimized (or non-optimized) radiation treatment plans developed for other patients. By one approach these radiation treatment plans were developed for use at the radiation treatment platform 114 described above. By another approach, in lieu of the foregoing or in combination there with, these radiation treatment plans were developed in other locations, such as but not limited to other treatment facilities and or academic/research facilities.

In this example, the training corpus includes some, but not all, possible patient volumes of interest. For example, part or all of the patient's lungs may comprise volumes of interest but the training corpus does not include content specific to lungs.

Figure 3:
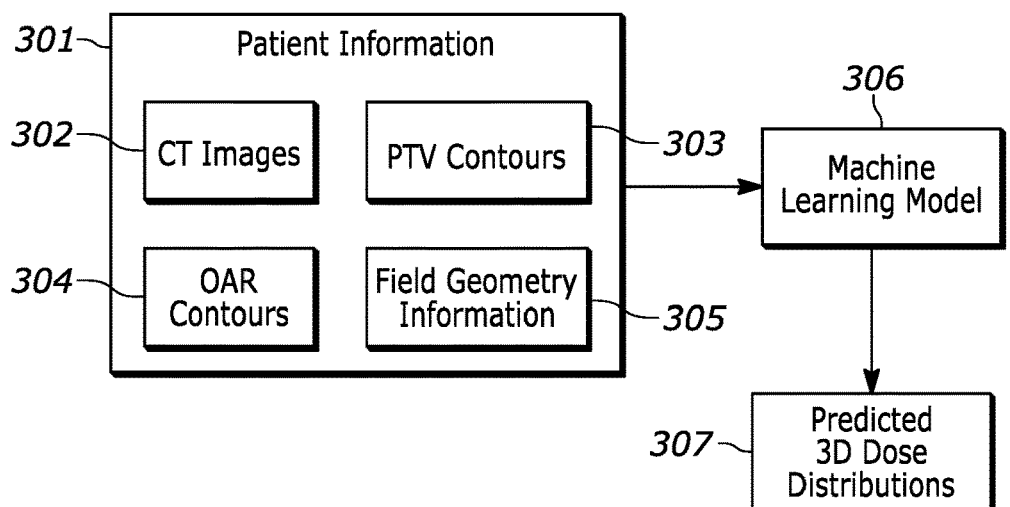
FIG. 3 comprises a block diagram as configured in accordance with various embodiments of these teachings.

At block 202, this process provides information regarding the patient themselves. In this example this patient information includes information regarding at least one volume of interest for the patient that was not represented in the training corpus. Again for the sake of illustration, that at least one volume of interest may comprise part or all of the patient's lung tissue. Referring momentarily to FIG. 3, the patient information 301 may include (but is not necessarily limited to) at least one computed tomography image 302, at least one patient treatment volume contour 303, at least one organ-at-risk contour 304, and field geometry information 305 (including, for example, directional information pertaining to incoming radiation).

With continued reference to both FIGS. 2 and 3, at block 203, this process 200 provides for inputting the foregoing information 301 regarding the patient to the radiation treatment plan three-dimensional dose prediction machine learning model 306 to thereby generate predicted three-dimensional dose distributions 307 for the at least one volume of interest for the patient that was not represented in the training corpus. Continuing with the example noted above, this can comprise providing a predicted three-dimensional dose distribution for lung tissue of the patient that was not represented in the training corpus.

Figure 4:
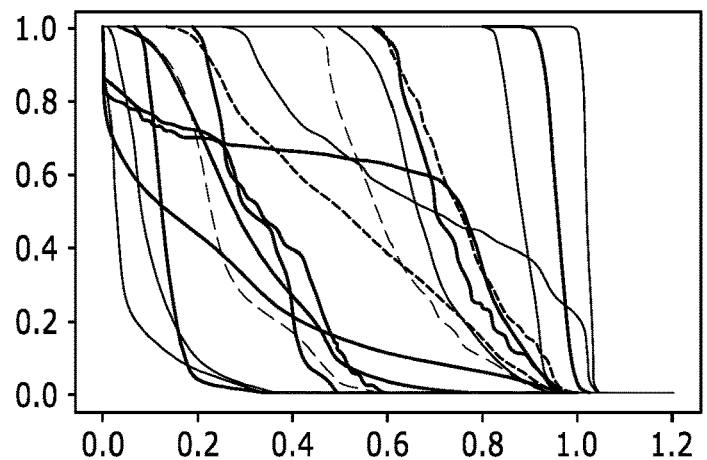
FIG. 4 comprises a graph as configured in accordance with various embodiments of these teachings.
Figure 5:
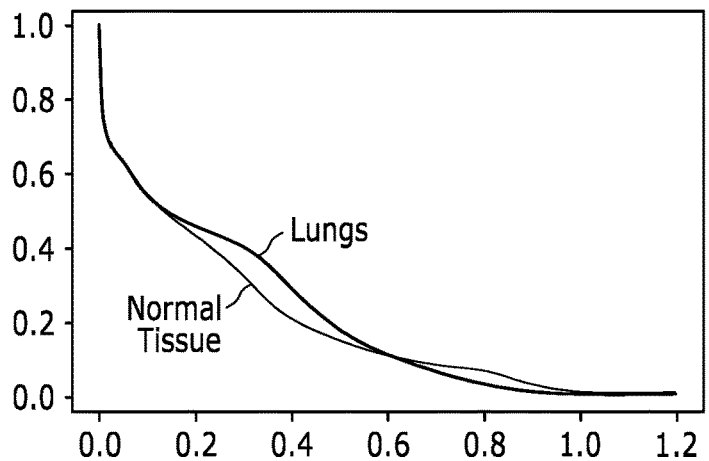
FIG. 5 comprises a graph as configured in accordance with various embodiments of these teachings.

FIGS. 4 and 5 present illustrative examples in these regards. In FIG. 4, dose volume histograms (DVH's) 400 are provided for various volumes of interest that were represented in the training corpus, while FIG. 5 presents dose volume histograms 500 for two volumes of interest that were not represented in the training corpus.

DVH's typically represent three-dimensional dose distributions in a graphical two-dimensional format (the three-dimensional dose distributions being created, for example, in a computerized radiation-treatment planning system based on a three-dimensional reconstruction of an X-ray computed tomography scan and study). The "volume" referred to in DVH analysis can be, for example, the radiation-treatment target, a healthy organ located near such a target, an arbitrary structure, and so forth.

DVH's are often visualized in either of two ways: as differential DVH's or as cumulative DVH's. With differential DVH's column height for a given dose bin corresponds to the volume of the structure that receives that dose. Bin doses typically extend along the horizontal axis while structure volumes (either percent or absolute volumes) extend along the vertical axis.

A cumulative DVH is typically plotted with bin doses along the horizontal axis but has a column height for the first bin that represents the volume of structure(s) that receive greater than or equal to that dose. The column height of the second bin then represents the volume of structure(s) that receive greater than or equal to that dose, and so forth. With high granularity a cumulative DVH often appears as a smooth line graph. For many application settings cumulative DVH's are preferred over differential DVH's but this process 200 can accommodate either approach.

By one approach, if desired and as represented at optional block 204, this process 200 will accommodate generating at least one dosimetric parameter for the at least one volume of interest for the patient that was not represented in the training corpus as a function of the predicted three-dimensional dose distribution. These teachings will accommodate a variety of dosimetric parameters. Some beneficial examples include, but are not limited to, a dose volume histogram, one or more maximum dose levels within a given contour, a maximum dose level for a target structure, mean dose levels within a given contour, dose-volume points, a homogeneity index for target coverage, a generalized equivalent uniform dose, and a conformity index.

As illustrated at optional block 205, by one approach this process 200 will accommodate automatically generating an optimization objective for the at least one volume of interest for the patient that was not represented in the training corpus as a function of the predicted three-dimensional dose distribution for the at least one volume of interest for the patient that was not represented in the training corpus. Those skilled in the art will understand that radiation treatment plans are typically based upon so-called objectives, at least some of which are typically derived from a prescribing physician's treatment instructions that specify clinical metrics for goals pertaining at least to the patient's treatment volume and sometimes to adjacent so-called organs-at-risk (OAR) as well. Generally speaking, optimization objectives are used by the optimizer as the building blocks of a cost function. In particular, a desired dose distribution corresponds to the microscopic state that minimizes these user-defined cost functions.

At optional block 206, this process 200 can provide for optimizing a radiation treatment plan 113 for the patient as a function of optimization objectives (including, when available, the automatically generated optimization objective described above). At optional block 207, this process can provide for administering therapeutic radiation to the patient as a function of the radiation treatment plan 113 utilizing, for example, the above-described radiation treatment platform 114.

By one approach, these teachings will accommodate non-biological structures. In particular, an application setting where the aforementioned information regarding the patient comprises information regarding a non-biological structure while the training corpus does not include the non-biological structure. In such a case, the foregoing process 200 can comprise inputting the information regarding the non-biological structure to the radiation treatment plan three-dimensional dose prediction machine learning model and generating predicted three-dimensional dose distributions that include at least one predicted three-dimensional dose distribution for that non-biological structure. Various non-biological structures can be so accommodated, including non-biological structures that are implanted or otherwise positioned within a patient's body as well as non-biological structures that are disposed externally to the patient's body. It will be understood that non-biological structures can comprise any physical object that is not a natural part of the patient's body.

As one illustrative example in these regards, consider the case where the non-biological structure is not very close to the tumor site, but the planner is still interested in seeing the dose distribution for that region. For instance, if the patient has a pacemaker and the tumor is not very close to the hart, but the planner wants to see how much radiation the pacemaker receives to make sure that the pacemaker will not be damaged or that the treatment is not delivered directly through the pacemaker (which might change the dose distribution since the pacemaker will likely have a different density than the surrounding tissue). In this case, one can apply the above-described model (i.e., a model trained on a training set without this non-biological structure) and nevertheless obtain a useful dose distribution for the region that contains the pacemaker.

These teachings permit using a three-dimensional dose prediction machine learning model to compute estimates of dose volume histograms or other dosimetrical parameters for any volume of interest that can be defined after the model training. This includes target structures, organs, normal tissue, or any volume created for the purpose of optimization.

Because the described three-dimensional dose prediction machine learning model outputs a full three-dimensional dose distribution map (or maps), this approach serves to compute dose estimates and set optimization objectives for any three-dimensional volume, including volumes not included in the initial training process of the model.

Those skilled in the art will appreciate that these full three-dimensional distribution maps provide richer content than mere dose-volume estimates, including spatial information for certain dose features. For instance, this information can identify the region of a given organ-at-risk where higher dose levels are observed, or the region of a target in which cold spots are observed. Such spatial information can be important, sometimes differentiating between a clinically acceptable plan and an unacceptable plan. For example, in a case with multiple brain tumors, a clinical plan that delivers higher dose levels in brain regions very close to the tumors may be clinically acceptable while hotter regions that are further from the location of the targets may not be clinically acceptable. Such spatial information cannot be captured by DVH-based optimization objectives, but can be well illustrated by the three-dimensional dose distribution maps offered via these teachings.

Those skilled in the art will recognize that a wide variety of modifications, alterations, and combinations can be made with respect to the above-described embodiments without departing from the scope of the invention, and that such modifications, alterations, and combinations are to be viewed as being within the ambit of the inventive concept.

What is claimed is:

1. A method to facilitate generating a radiation treatment plan for a patient, the method comprising:
   providing a radiation treatment plan three-dimensional dose prediction machine learning model that has been trained using a training corpus that includes a plurality of radiation treatment plans that are not specific to the patient;
   providing information regarding the patient, wherein the patient information includes information regarding at least one organ-at-risk for the patient that was not represented in the training corpus;
   inputting the information regarding the patient to the radiation treatment plan three-dimensional dose prediction machine learning model and generating predicted three-dimensional dose distributions that include a predicted three-dimensional dose distribution for at least one organ-at-risk for the patient that was not represented in the training corpus.

2. The method of claim 1 wherein the radiation treatment plan three-dimensional dose prediction machine learning model comprises a neural network machine learning model.

3. The method of claim 2 wherein the neural network machine learning model comprises a convolutional neural network.

4. The method of claim 1 wherein the information regarding the patient comprises:
   at least one computed tomography image;
   at least one patient treatment volume contour;
   at least one organ-at-risk contour; and
   field geometry information.

5. The method of claim 1 further comprising:
   generating at least one dosimetric parameter for the at least one organ-at-risk for the patient that was not represented in the training corpus as a function of the predicted three-dimensional dose distribution.

6. The method of claim 5 wherein the at least one dosimetric parameter comprises at least one of:
   a dose volume histogram;
   maximum dose levels within a given contour;
   a minimum dose level for a target structure;
   mean dose levels within a given contour;
   dose-volume points;
   a homogeneity index for target coverage;
   a generalized equivalent uniform dose;
   a conformity index.

7. The method of claim 1 wherein:
   the information regarding the patient comprises information regarding a non-biological structure;
   the training corpus does not include the non-biological structure;
   and wherein the method further comprises:
   inputting the information regarding the non-biological structure to the radiation treatment plan three-dimensional dose prediction machine learning model and generating predicted three-dimensional dose distributions that include a predicted three-dimensional dose distribution for the non-biological structure.

8. The method of claim 1 further comprising:
   automatically generating an optimization objective for the at least one organ-at-risk for the patient that was not represented in the training corpus as a function of the predicted three-dimensional dose distribution for the at least one organ-at-risk for the patient that was not represented in the training corpus.

9. The method of claim 8 further comprising:
optimizing a radiation treatment plan for the patient as a function of the optimization objective.

10. The method of claim 9 further comprising:
administering therapeutic radiation to the patient as a function of the radiation treatment plan.

11. An apparatus to facilitate generating a radiation treatment plan for a patient, the apparatus comprising:
a memory having a radiation treatment plan three-dimensional dose prediction machine learning model stored therein, wherein the radiation treatment plan three-dimensional dose prediction machine learning model has been trained using a training corpus that includes a plurality of radiation treatment plans that are not specific to the patient;
a control circuit operably coupled to the memory and configured to:
receive information regarding the patient, wherein the patient information includes information regarding at least one organ-at-risk for the patient that was not represented in the training corpus;
input the information regarding the patient to the radiation treatment plan three-dimensional dose prediction machine learning model and generate predicted three-dimensional dose distributions that include a predicted three-dimensional dose distribution for the at least one organ-at-risk for the patient that was not represented in the training corpus.

12. The apparatus of claim 11 wherein the radiation treatment plan three-dimensional dose prediction machine learning model comprises a neural network machine learning model.

13. The apparatus of claim 12 wherein the neural network machine learning model comprises a convolutional neural network.

14. The apparatus of claim 11 wherein the information regarding the patient comprises:
at least one computed tomography image;
at least one patient treatment volume contour;
at least one organ-at-risk contour; and
field geometry information.

15. The apparatus of claim 11 wherein the control circuit is further configured to:
generating at least one dosimetric parameter for the at least one organ-at-risk for the patient that was not represented in the training corpus as a function of the predicted three-dimensional dose distribution.

16. The apparatus of claim 15 wherein the at least one dosimetric parameter comprises at least one of:
a dose volume histogram;
maximum dose levels within a given contour;
a minimum dose level for a target structure;
mean dose levels within a given contour;
dose-volume points;
a homogeneity index for target coverage;
a generalized equivalent uniform dose;
a conformity index.

17. The apparatus of claim 11 wherein:
the information regarding the patient comprises information regarding a non-biological structure;
the training corpus does not include the non-biological structure;
the control circuit is further configured to input the information regarding the non-biological structure to the radiation treatment plan three-dimensional dose prediction machine learning model and generate predicted three-dimensional dose distributions that include a predicted three-dimensional dose distribution for the non-biological structure.

18. The apparatus of claim 11 wherein the control circuit is further configured to:
automatically generate an optimization objective for the at least one organ-at-risk for the patient that was not represented in the training corpus as a function of the predicted three-dimensional dose distribution for the at least one organ-at-risk for the patient that was not represented in the training corpus.

19. The apparatus of claim 18 wherein the control circuit is further configured to:
optimize a radiation treatment plan for the patient as a function of the optimization objective.

20. The apparatus of claim 19 further comprising:
a radiation treatment platform operably coupled to at least receive the radiation treatment plan and configured to administer therapeutic radiation to the patient as a function of the radiation treatment plan.

* * * * *